US00PP28377P2

(12) United States Plant Patent
Klemm et al.

(10) Patent No.: US PP28,377 P2
(45) Date of Patent: Sep. 12, 2017

(54) ***DIANTHUS* PLANT NAMED 'KLEDG15176'**

(50) Latin Name: ***Dianthus* sp.**
Varietal Denomination: KLEDG15176

(71) Applicant: Klemm+Sohn GmbH & Co KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 77 days.

(21) Appl. No.: 14/998,796

(22) Filed: Feb. 17, 2016

(51) Int. Cl.
*A01H 5/02* (2006.01)

(52) U.S. Cl.
USPC ..... Plt./277

(58) Field of Classification Search
USPC ..... Plt./277
See application file for complete search history.

(56) References Cited

PUBLICATIONS

UPOV hit on *Dianthus* plant named 'KLEDG15176', CA PBR 15-8574, published Apr. 2, 2015.*

* cited by examiner

*Primary Examiner* — Anne Grunberg
(74) *Attorney, Agent, or Firm* — Barbara Campbell; James M. Weatherly; Cochran Freund & Young, LLC

(57) ABSTRACT

A new *Dianthus* plant particularly distinguished by bi-color dark purple-pink, semi-double flowers, and an upright and bushy habit, is disclosed.

1 Drawing Sheet

Genus and species: *Dianthus* sp.
Variety denomination: 'KLEDG15176'.

BACKGROUND OF THE NEW PLANT

The present invention comprises a new and distinct variety of *Dianthus*, botanically known as *Dianthus* sp., and hereinafter referred to by the variety name 'KLEDG15176'. 'KLEDG15176' originated from a cross-combination in June 2010 between the proprietary *Dianthus* female parent 'DSS-2009-0511' (unpatented) and the proprietary *Dianthus* male parent 'DSS-2007-0020' (unpatented) in Stuttgart Germany.

In July 2010 seed was collected from the cross-combination between the two *Dianthus* parental lines. The seeds were sown and plants were grown for evaluation in Stuttgart, Germany. A single plant was selected in May 2011 and was subsequently named 'KLEDG15176'. In July 2011, 'KLEDG15176' was first vegetatively propagated by stem and tip cuttings. 'KLEDG15176' was found to reproduce true to type in successive generations of asexual propagation via cuttings.

SUMMARY

The following are the most outstanding and distinguishing characteristics of this new variety when grown under normal horticultural practices in Stuttgart, Germany.

1. Bi-color dark purple-pink, semi-double flowers; and
2. An upright and bushy habit.

CROSS-REFERENCE TO RELATED APPLICATIONS

An application for Plant Breeders Rights in Canada was filed on Apr. 2, 2015, Application No. 15-8574.

DESCRIPTION OF THE PHOTOGRAPH

This new *Dianthus* plant is illustrated by the accompanying photograph of a plant approximately 8-weeks-old and grown in a glass greenhouse in Stuttgart, Germany. The photograph shows the whole plant, including the flowers and foliage and buds and was taken in May 2014 in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEDG15176'. The data which define these characteristics were collected from asexual reproductions carried out in Stuttgart, Germany, and Latina, Italy. The Netherlands. Data was collected on plants grown 7-months after planting and grown in a greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* sp.
- *Common*.—Pot carnation.
- *Designation*.—'KLEDG15176'.

Parentage:
- *Female parent*.—The proprietary *Dianthus* 'DSS-2009-0511' (unpatented).
- *Male parent*.—The proprietary *Dianthus* 'DSS-2007-0020' (unpatented).

Plant:
- *Propagation type*.—Vegetative cuttings.
- *Time to produce a rooted young plant*.—20 days.
- *Root description*.—White-cream, RHS 155D, medium thickness.

*Rooting habit*.—Freely-branching.
*Plant form*.—Upright and bushy.
*Plant height*.—15.0 cm.
*Plant diameter or spread*.—18.0 cm.

Lateral branches:
*Length*.—6.0 cm to 10.0 cm.
*Diameter*.—2.0 cm.
*Internode length*.—0.5 cm to 1.0 cm.
*Number of internodes per branch/stem*.—3 to 4.
*Node length*.—0.4 cm.
*Node diameter*.—0.4 cm.
*Texture*.—Smooth.
*Color*.—RHS 137A to RHS 137B.
*Branch/stem*.—Solid.

Foliage:
*Arrangement*.—Opposite.
*Length*.—4.0 cm to 6.0 cm.
*Width*.—0.4 cm to 0.7 cm.
*Shape*.—Lanceolate.
*Apex*.—Acute.
*Base*.—Obtuse.
*Margin*.—Entire.
*Texture* (*both upper and lower surfaces*).—Smooth.
*Immature leaf color*.—Upper surface: RHS 137B. Lower surface: RHS 137D.
*Mature leaf color*.—Upper surface: RHS 137A. Lower surface: RHS 137D.
*Venation pattern*.—Not strong, pinnate.
*Venation color* (*both surfaces*).—RHS 137B.

Flowers:
*Flower type and habit*.—Round, semi-double, and continuous flowering.
*Fragrance*.—Present, strong.
*Natural flowering season*.—Spring to autumn.
*Position of flowers relative to the foliage*.—Slightly above.
*Number of flowers per spray*.—4 to 6.
*Flower longevity on the plant*.—More than 10 days.
*Buds*.—Length: 1.0 cm to 2.0 cm. Diameter: 0.5 cm to 0.7 cm. Shape: Ovate-cylindrical. Color: RHS 137A. Extrusion of the styles at the bud stage: Absent.
*Corolla*.—Quantity of petals and arrangement: 8 petals and petaloids. Corolla height: 1.5 cm. Petal length: 2.5 cm. Petal width: 1.7 cm. Petal shape: Drop-shaped. Petal apex: Obtuse. Petal base: Peaked. Petal margin: Entire. Depth of petal margin: Very shallow. Petal texture (both upper and lower surfaces): Smooth. Petal color: Immature: Upper surface: RHS 63C and RHS 59C. Lower surface: RHS 59C. Mature: Upper surface: RHS 63C and RHS 59D. Lower surface: RHS 59D.
*Calyx*.—Quantity of sepals and arrangement: Composed of 5 sepals. Shape: Cylindrical. Calyx height: 2.0 cm. Calyx diameter (at the apex): 0.6 cm. Sepal texture (both upper and lower surfaces): Smooth. Sepal color: Upper surface: RHS 137A. Lower surface: RHS 137D.

Peduncles:
*Length*.—6.0 cm to 8.0 cm.
*Diameter*.—0.1 cm to 0.2 cm.
*Strength*.—Moderate.
*Texture*.—Smooth.
*Color*.—RHS 137B.

Reproductive organs:
*Stamens*.—Quantity per flower: Approximately 5 to 6. Filament length: 0.6 cm. Filament color: RHS 76D. Anther length: 0.2 cm. Anther diameter: 0.08 cm. Anther color: RHS 69D. Pollen amount: Moderate to abundant.
*Pistils*.—Quantity per flower: 1. Pistil length: 2.0 cm. Style length: Approximately 1.5 cm. Style color: RHS 63C. Stigma shape: Filamentous. Stigma color: RHS 59C. Ovary size: 0.5 cm. Ovary shape: Ovate. Ovary color: RHS 142C.

Fruit and seed set: Seed sometimes observed; additional information on seed not available.

Disease and pest/insect resistance: No special observations were made.

COMPARISON WITH PARENTAL LINES AND KNOWN VARIETY

'KLEDG15176' is a distinct variety of *Dianthus* and is distinguished from the parental lines as described in Table 1

TABLE 1

Comparison with Parental Lines

| Characteristic | 'KLEDG15176' | Female parent 'DSS-2009-0511' | Male parent 'DSS-2007-0020' |
|---|---|---|---|
| Growth habit | Medium | Strong | Strong |
| Flower color | Bi-color dark purple/pink | Dark pink | Violet |

'KLEDG15176' is a distinct variety of *Dianthus* and is most similar to the commercial *Dianthus* variety 'KLEDG13146' (U.S. Plant Pat. No. 25,877), also commercially known as EVERLAST 'Lavender Lace'. Differences between the varieties are described in Table 2.

TABLE 2

Comparison with Similar Variety

| Characteristic | 'KLEDG15176' | 'KLEDG13146' |
|---|---|---|
| Flower type | Semi-double | Single |
| Flower color | Bi-color dark purple/pink | Violet-purple |

We claim:

1. A new and distinct variety of *Dianthus* plant named 'KLEDG15176' as illustrated and described herein.

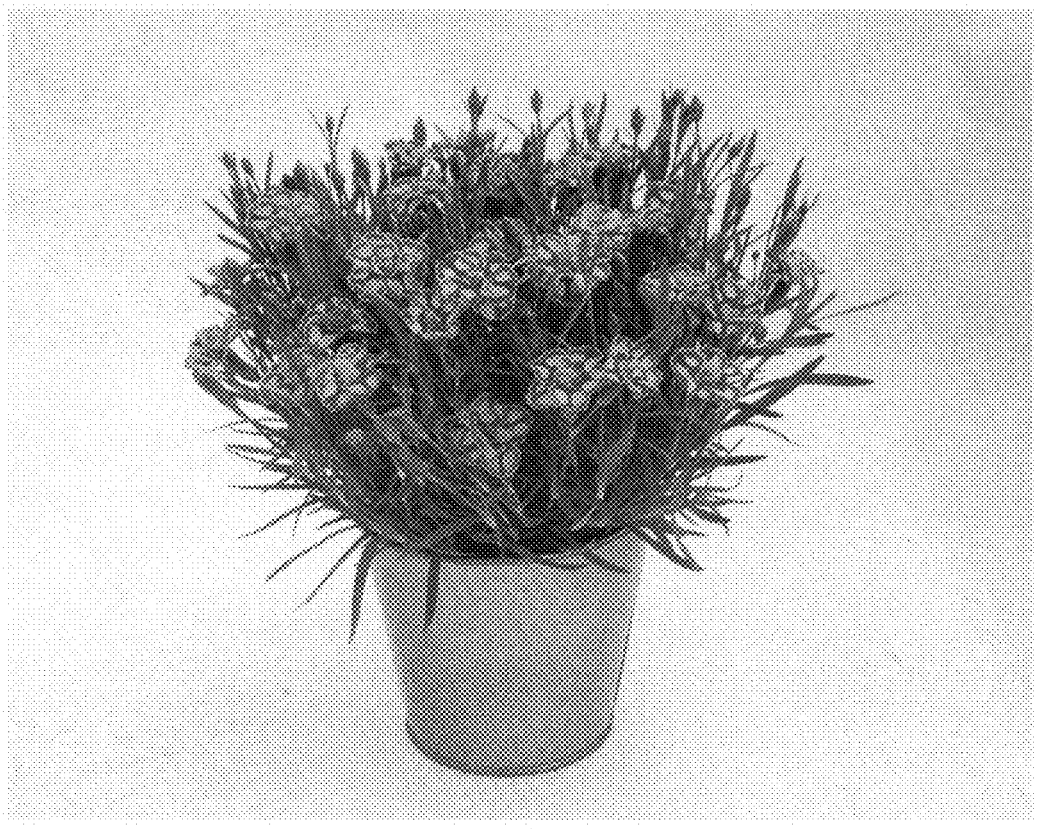

* * * * *